United States Patent [19]

Sauter et al.

[11] Patent Number: 5,403,305
[45] Date of Patent: Apr. 4, 1995

[54] MITRAL VALVE PROSTHESIS ROTATOR

[75] Inventors: Joseph A. Sauter; Louis A. Campbell; John C. Budd, all of Austin, Tex.

[73] Assignee: Carbomedics, Inc.

[21] Appl. No.: 18,882

[22] Filed: Apr. 8, 1993

[51] Int. Cl.$^6$ .................. A61F 2/24; A61F 2/46; A61B 17/00
[52] U.S. Cl. .................. 606/1; 623/2; 623/66
[58] Field of Search .................. 623/2, 900, 66; 606/1, 606/99, 108, 159

[56] References Cited

U.S. PATENT DOCUMENTS

| | | | |
|---|---|---|---|
| 3,336,927 | 8/1967 | Klebanoff | 606/108 |
| 3,860,005 | 1/1975 | Anderson et al. | 606/1 |
| 4,065,816 | 1/1978 | Sawyer et al. | 623/2 |
| 4,182,446 | 1/1980 | Perry | 623/2 X |
| 4,211,325 | 7/1980 | Wright | 623/2 X |
| 4,585,453 | 4/1986 | Martin et al. | 623/2 |
| 4,655,218 | 4/1987 | Kulik et al. | 623/2 X |
| 4,679,556 | 7/1987 | Lubock et al. | 606/1 |
| 4,683,883 | 8/1987 | Martin | 623/2 X |
| 4,765,334 | 8/1988 | Weiss | 606/108 |
| 4,798,193 | 1/1989 | Giesv et al. | 606/108 |
| 4,865,600 | 9/1989 | Carpentier et al. | 623/2 |
| 4,878,494 | 11/1989 | Phillips et al. | 128/334 R |
| 5,011,481 | 4/1991 | Myers et al. | 623/2 X |
| 5,030,219 | 7/1991 | Matsen, III et al. | 606/53 |
| 5,041,130 | 8/1991 | Cosgrove et al. | 623/2 |
| 5,154,719 | 10/1992 | Cotrel | 606/73 |
| 5,163,955 | 11/1992 | Love et al. | 623/2 |
| 5,197,979 | 3/1993 | Quintero et al. | 623/2 |
| 5,236,450 | 8/1993 | Scott | 623/2 |
| 5,290,294 | 3/1944 | Cox et al. | 606/108 |

Primary Examiner—David Isabella
Assistant Examiner—Laura Fossum
Attorney, Agent, or Firm—John R. Merkling

[57] ABSTRACT

A prosthetic heart valve rotator with an eccentric socket attached to a bendable shaft. The heart valve is manipulated by a rotator head which is attached to the socket in any of a plurality of selectable angular positions. The rotator head is held in the socket by a spring which circumscribes the socket, thereby reducing stress in the spring.

23 Claims, 3 Drawing Sheets

MITRAL VALVE PROSTHESIS ROTATOR

BACKGROUND OF THE INVENTION

1. Field of the Invention

Our invention pertains to apparatus for manipulating mechanical heart valve prostheses and in particular, for manipulating heart valve prostheses implanted at the site of the mitral valve.

2. Description of Related Art

Heart valve prostheses may be classified into two general categories: bioprosthetic heart valves and mechanical heart valves. By bioprosthetic heart valves we mean heart valves with generally flexible leaflets comprised of biological tissue. These include leaflets formed of treated human valve tissue (allografts), or of treated porcine or other non-human tissue (xenografts). By mechanical heart valves we mean heart valves made primarily from non-biologic materials, for example, metals, ceramics or polymers. These include ball valves and valves having one, two or more rigid leaflets. One popular valve design for a mechanical heart valve prosthesis includes an annular valve body in which a pair of opposed leaflet occluders are pivotally mounted. The occluders are movable between a closed, mated position, blocking blood flow in an upstream direction, and minimizing regurgitation, and an open position, allowing blood flow in a downstream direction. The annular valve body is surrounded by a sewing ring which permits the surgeon to suture the valve in place at the site of an excised valve.

When a valve is placed within the heart, it must be accurately oriented to maximize its function. Particularly in mechanical heart valves, the orientation of the leaflets is critical since their opening and closing pathways may otherwise impinge on the surrounding cardiac walls, the walls of arteries within which the valve is placed, or the residual valvular structures including the tendeae chordae and papillary muscles. This difficulty becomes particularly acute in the placement of a heart valve in the position of the mitral valve in the heart. When replacing this valve, a surgeon will frequently expose the posterior side of the patient's heart and enter the heart through walls of the left atrium and sometimes through the right atrium. It is desirable to place the valve accurately within the cramped confines of the heart while leaving room for the surgeon to sew the valve in place. Moreover, accurate sizing of the prosthetic heart valve is very important for the long-term viability of the prosthesis. The size of the heart valve can frequently not be determined exactly until the site of the valve has been exposed. Thus, it is a frequent occurrence that a different sized valve may be selected by a surgeon interoperatively.

In the past surgeons most often used a left thoracotomy surgical procedure to reach the heart which allows a straight line of access to the mitral valve. Common practice, however, has shifted away from the thoracotomy which involves resecting a rib and provides poor access to the aorta. Many surgeons today perform a median sternotomy, bisecting the rib cage by sawing the sternum in half. This approach provides clear access to the aorta and right atrium, allowing the surgeon to easily place the patient on by-pass, work on the aortic valve and either the pulmonary or tricuspid heart valve. Unfortunately, this approach does not provide easy access to the mitral valve, forcing the surgeon to reach behind the heart or through the right atrium into the left atrium.

SUMMARY OF THE INVENTION

To aid in the rotation of a heart valve within a sewing ring in the mitral position, we have invented a heart valve prosthesis rotator. The rotator of our invention has an annealed stainless steel shaft which can be bent by the surgeon interoperatively, but which will retain its shape sufficiently to allow the manipulation of a heart valve engaged by the rotator. The rotator has an eccentric socket attached to the stem which displaces the structure engaging the heart valve prosthesis from an axis of the stem. This allows additional clearance when the heart valve is in position so that the surgeon can approach the valve from any orientation, even in cases of extremely small atriums, with minimum damage to the atrial wall. A rotator head engages the prosthetic heart valve and is attached to the eccentric socket. The socket and head snap together with a hexagonal bore and hexagonal post respectively. Because of the hexagonal configuration of the post and bore, the rotator head can be oriented quickly and replicably attached with respect to the eccentric socket. Moreover, different size heads can be substituted onto the rotator by replacing the rotator head which engages the prosthesis on the eccentric socket.

With the foregoing in mind, it is principal object of our invention to provide a heart valve prosthesis rotator with a deformable shaft.

It is further object of our invention to provide a rotator with an eccentric socket and head which engage the prosthesis.

It also an object of our invention to provide a rotator with replaceable rotator heads for different size rotator head and prosthesis combinations.

Another object of our invention is to provide a socket and rotator head wherein rotator heads may be substituted on the socket at a desired angular orientation between the eccentric socket and rotator head.

These and other objects and features of our invention will be apparent to those skilled in the art from the following detailed description, taken with reference to the accompanying drawings.

DETAILED DESCRIPTION OF OUR PREFERRED EMBODIMENT

Figures 1, 2:
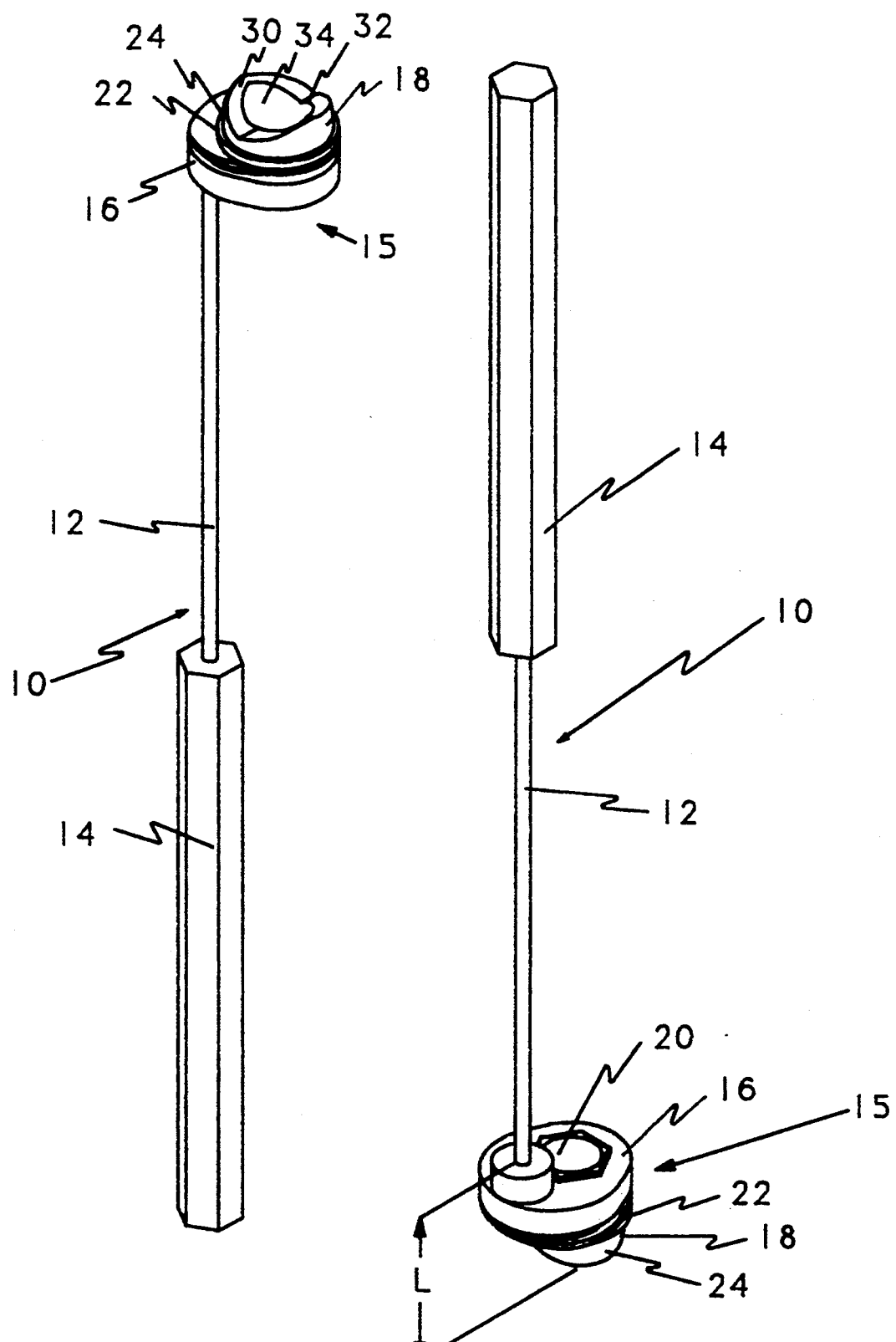
FIG. 1 is a perspective view of a heart valve rotator according to our invention.
FIG. 2 is an inverted perspective view of the rotator of FIG. 1.

Referring now to the drawings, a heart valve prosthesis rotator, generally designated 10, is shown in perspective view in FIG. 1. The rotator 10 comprises an annealed stainless steel shaft 12 with a plastic handle 14 at a distal end thereof. "Proximal" denotes a part of an apparatus which is relatively close to the heart when in use, as is customary in cardiovascular surgery. "Distal" denotes a part remote from the heart and, consequently near the physician. At a proximal end of the shaft 12 is a valve engaging means 15 comprising an eccentric socket 16 supporting a rotator head 18.

Mechanical heart valves generally comprise an annular body containing one, two or more leaflets or occluders. Leaflets move from a closed position impeding the flow of blood to an open position permitting flow of blood. In our preferred embodiment, a rotator head for a bileaflet mechanical heart valve is described. Those skilled in the art, however, will recognize that rotator heads may be constructed for single leaflet valves as well as for trileaflet or a multiple leaflet valves without departing from the spirit or teachings of our invention.

Figure 5:
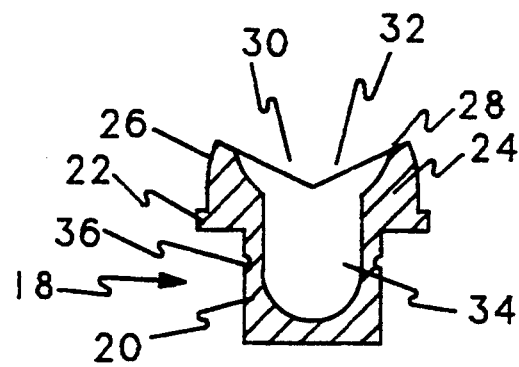
FIG. 5 is a through section of the rotator head of FIG. 3 taken along line 5—5.

The rotator head is seen in through section in FIG. 5. It comprises a hexagonal post 20 which attaches to the eccentric socket as more fully described below. A lip 22 separates the post 20 from a crown 24. The crown 24 carries the valve prosthesis. The crown is generally cylindrical in shape with a chamfer or curve 26 near a proximal end 28. The proximal end 28 is formed by two obliquely intersecting planes 30, 32. The planes 30, 32 support the inflow faces of two leaflets of a bileaflet heart valve (not shown) and hold the leaflets in closed position while the valve is being rotated within the heart. In the mitral position, the inflow faces of the heart valve will be adjacent the left atrium, while the outflow faces will be implanted adjacent the left ventricle. In our preferred embodiment, the rotator head is formed of thermo setting plastic to minimize the possibility of damage to the leaflets of the prosthesis. For ease of molding, a cavity 34 is provided within the rotator head. The cavity is shaped so that the walls of the rotator head are of relatively uniform thickness. This minimizes stresses and deformation during molding. A groove 36 encircles the post 20 for snapping the rotator head into the eccentric socket, as will be more fully described below.

Figures 3, 4:
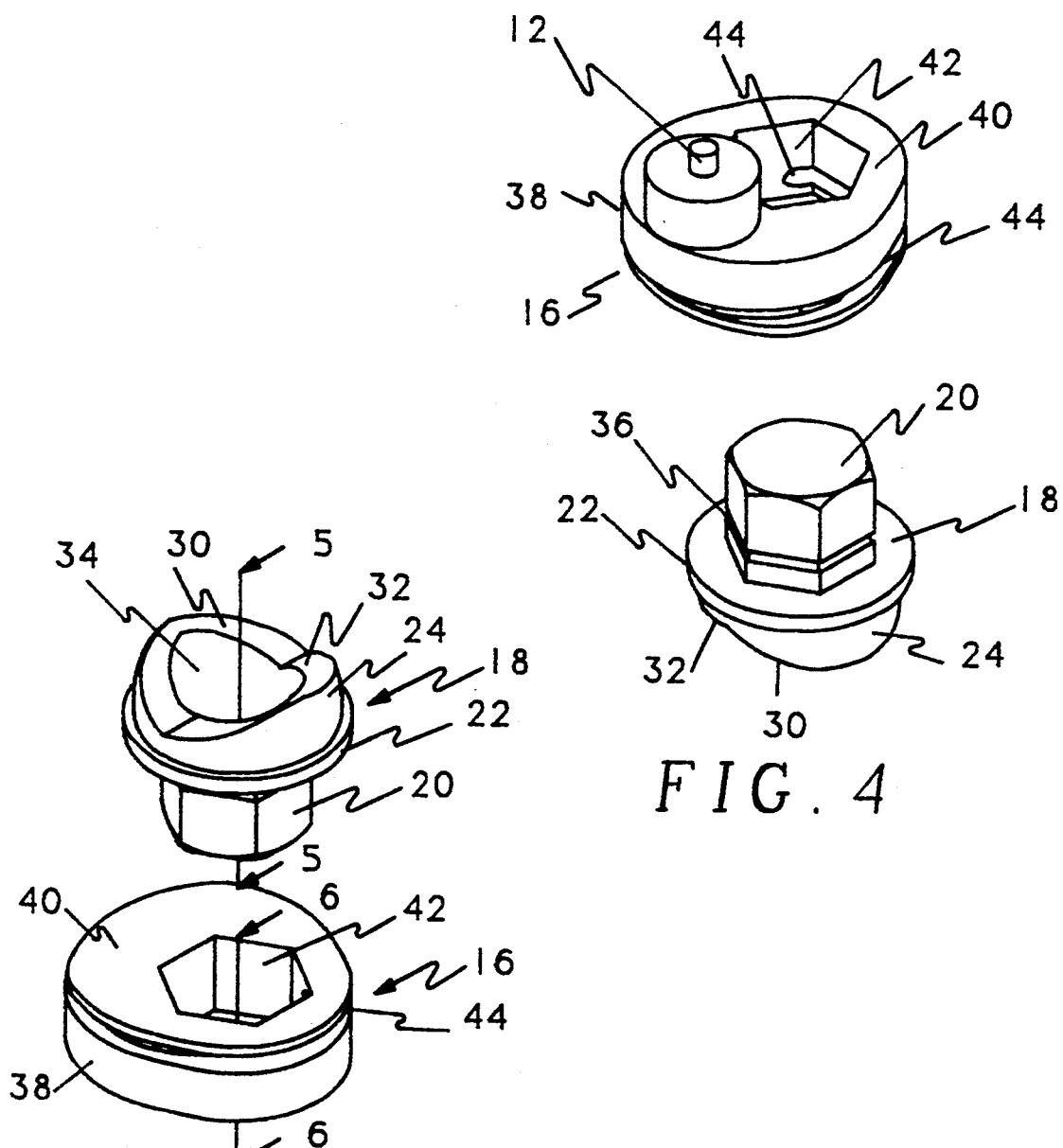
FIG. 3 is an exploded, enlarged perspective view of a rotator head and eccentric socket for the rotator of FIG. 1.
FIG. 4 is an inverted view of the socket and rotator head of FIG. 3.
Figure 8:
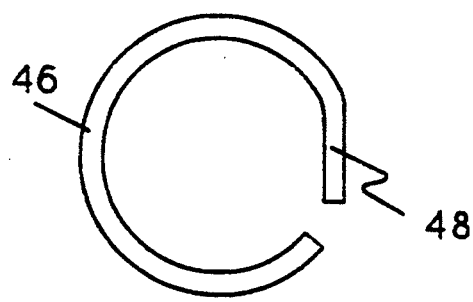
FIG. 8 is a top plan view of a spring used in the eccentric socket.
Figure 7:
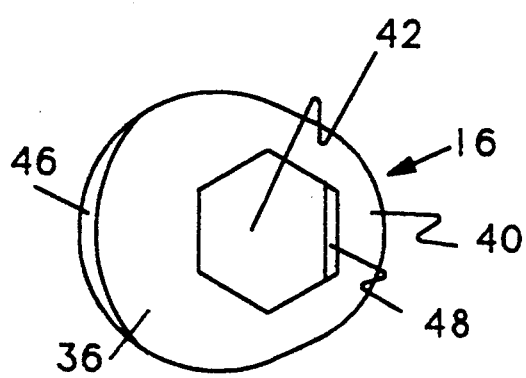
FIG. 7 is a top plan view of the eccentric socket of FIG. 3.
Figure 6:
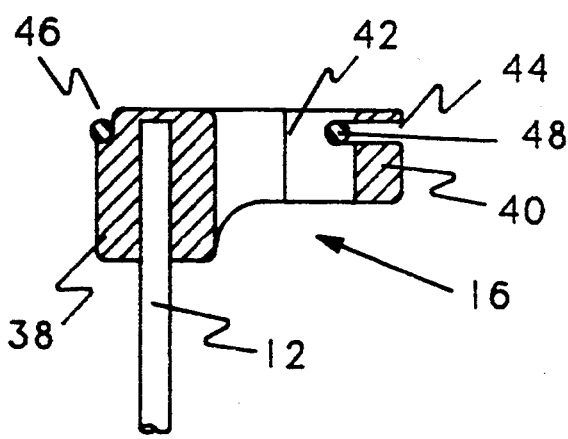
FIG. 6 is a through section of the eccentric socket of FIG. 3 taken along line 6—6.

The eccentric socket 16 is also molded of plastic and is attached to a proximal end of the annealed shaft 12. The socket 16 comprises a body 38 connected to the shaft with a lateral ledge 40 extending generally perpendicularly with respect to the shaft. An hexagonal through bore 42 extends through the ledge 40 and receives the hexagonal post 20. When the head 18 and socket 16 are assembled, the post 20 protrudes above the ledge 40, as shown in FIG. 2. Pressing on the post disengages the head 18 from the socket 16. A lateral slot 44 is formed in the ledge and extends around the ledge 40, forming an exposed lip 46 on the body 38 opposite the ledge 40. A "D" shaped, split retaining ring or spring 48 inserted both into the slot 44 and on the exposed lip 46 captures the hexagonal post of the rotator head by engaging the groove 36 mentioned above. The slot and lip generally define a "D" shaped seat for the retaining ring 44, when viewed from the top as, for example, in FIG. 7. The center of this seat is so orientated that the segment of the "D" ring intersects the hexagonal through bore 42, as can be seen in FIG. 4. This permits the retaining ring 48 to be exposed within the hexagonal through bore as seen in FIG. 7. When the rotator head is inserted into the eccentric socket, the retaining spring 48 will engage the groove 36, holding the head and socket together. Advantageously, this configuration produces a spring which deforms radially, so deflection is small with respect to the size of the spring and fatigue resistance is increased.

The valve engaging means 15 comprising, in combination, the eccentric socket 16 and the rotator head 18, has an overall proximal-to-distal length (dimension L in FIG. 2) of 3 cm or less. This is particularly important where a patient's heart is small, especially in children.

The preferred embodiment of our invention provides several advantages as a result of the features described above. Because the rotator head is detachable from the eccentric socket, multiple different valve sizes can be engaged with the same handle, stem and socket combination. The surgeon is able to bend the stem to obtain the best orientation for engagement of a valve. If the surgeon notes that a different size heart valve is required, the rotator head can be easily removed and a new rotator head for engaging a different size valve can be snapped into the eccentric socket. Because of the anti-rotation feature of the hexagonal post and hexagonal bore, the new rotator head can be placed in the correct orientation to engage the previously implanted valve. The stem will not need to be reshaped, but the valve can be rotated in position.

Even in a large heart, cardiac surgery by median sternotomy makes the availability of a bendable handle important. In cases where the heart is small, such as with children, the reduced length of the component that contacts the valve becomes very important because the atrium can be as small as a few centimeters in length.

Moreover, after the initial placement of the valve, the rotator head and can be incrementally rotated to engage the valve and to obtain the best overall orientation of the leaflets. This orientation can then be refined by bending the stem.

The foregoing description of a preferred embodiment of our invention is intended in all respects to be illustrative, and not restrictive, and it is intended that our invention be defined by the scope of the appended claims. Any variations which fall within the meaning and scope of equivalence of the claims are intended to be included herein.

We claim as our invention:

1. A surgical rotator for orienting a prosthetic mechanical heart valve in a mitral valve having an annular valve body with a central orifice therethrough, said rotator comprising, a handle having a distal end, a proximal end and a length extending therebetween, symmetrical about an axis means for engaging said heart valve, said means for engaging said heart valve being generally symmetrical about an axis, and means for connecting said proximal end of said handle and said means for engaging said heart valve with said axis of said handle lying generally parallel to said axis of said means for engaging said heart valve, and said axis of said handle being eccentrically offset from said axis of said means for engaging, said means for engaging and said means for connecting having a combined proximal-to-distal length small enough to fit within a thoracic cavity of a patient.

2. The rotator according to claim 1 wherein said proximal-to-distal length is 3 cm or less.

3. The rotator according to claim 1 further comprising a socket in said means for connecting said handle and said means for engaging said heart valve, said socket being spaced away from said proximal end of said handle and wherein said means for engaging said heart valve further comprises a rotator head, and means for releasably attaching said rotator head to said socket.

4. The rotator according to claim 3 wherein said proximal-to-distal length is 3 cm or less.

5. The rotator according to claim 3 wherein said connecting means comprises a flexible shaft.

6. The rotator according to claim 5 wherein the flexible shaft is comprised of annealed metal.

7. The rotator according to claim 3 further comprising means for selectively rotationally orienting said rotator head with respect to said eccentric socket in one of at least three radially distinct positions.

8. The rotator according to claim 1 wherein the connecting means comprise a flexible shaft.

9. The rotator according to claim 8 wherein the flexible shaft is comprised of annealed metal.

10. A rotator for orienting a prosthetic heart valve comprising a handle, and means for engaging said heart valve, said means for engaging said heart valve comprising connector means attached to said handle having first mating means thereon, a rotator head for engaging said heart valve and having thereon a congruent second mating means configured to engage said first mating means, and a spring circumferentially disposed about said first mating means and releasably engaging said second mating means for releasably attaching said rotator head to said connector means.

11. A rotator for orienting a prosthetic mechanical heart valve comprising an annular valve body with a central orifice therethrough, said rotator comprising, a handle having a distal end, a proximal end and a length extending therebetween, a rotator head for engaging said heart valve, said rotator head having a post thereon, and means for connecting said proximal end of said handle and said rotator head, said means for connecting having a junction where said proximal end of said handle joins said means for connecting, an eccentric socket in said means for connecting, said socket being offset perpendicularly to said length of said handle away from said junction and being configured to receive said post, and a spring circumferentially disposed about said socket for releasably engaging said post on at least one side thereof.

12. The rotator according to claim 11 wherein said rotator head is generally symmetrical about an axis and said proximal end of said handle is spaced away from said axis.

13. The rotator according to claim 12 wherein said socket is spaced away from said proximal end of said handle.

14. The rotator according to claim 13 wherein the socket includes a through bore.

15. The rotator according to claim 14 wherein the bore has a cross section of a regular polygon and wherein the shaft has a cross section of a congruent regular polygon.

16. The rotator according to claim 15 wherein the engaging means has an axial length of 3 cm or less.

17. The rotator according to claim 16 wherein the connecting means comprise a flexible shaft.

18. The rotator according to claim 17 wherein the flexible shaft is comprised of annealed metal.

19. A rotator for a prosthetic heart valve comprising a handle symmetrical about an axis, a rotator head for engaging said heart valve, and means attached to said handle for releasably connecting said rotator head in a selected one of at least three radially distinct originations about an axis, said axis of said rotator head being generally parallel to said axis of said handle and spaced a distance away from said axis of said handle, said distance being perpendicular to said axis of said handle.

20. The rotator according to claim 19 wherein said means for releasably connecting said rotator head comprise a socket in said means for releasably connecting said rotator head, and said rotator head comprises a post for insertion in said socket.

21. The rotator according to claim 20 wherein said means for releasably connecting said rotator head comprise a spring circumferentially disposed about said socket and releasably engaging said post on at least one side thereof.

22. The rotator according to claim 20 wherein said socket has a cross section of a regular polygon and wherein said post has a similar cross section of a congruent regular polygon.

23. The rotator according to claim 22 wherein said means for releasably connecting said rotator head comprise a spring circumferentially disposed about said socket and releasably engaging said post on at least one side thereof.

* * * * *